United States Patent [19]

Furminger et al.

[11] 4,158,054
[45] Jun. 12, 1979

[54] PREPARATION OF VIRUS SUB-UNIT VACCINES

[75] Inventors: Ian G. S. Furminger, Wirral; Margaret I. Brady, Lydiate, both of England

[73] Assignee: Duncan Flockhart & Co. Ltd., Edinburgh, Scotland

[21] Appl. No.: 879,386

[22] Filed: Feb. 21, 1978

Related U.S. Application Data

[63] Continuation of Ser. No. 680,756, Apr. 27, 1976, abandoned, which is a continuation of Ser. No. 515,467, Oct. 17, 1974, abandoned.

[30] Foreign Application Priority Data

Oct. 18, 1973 [GB] United Kingdom ............... 48685/73

[51] Int. Cl.$^2$ ...................... A61K 39/12; A61K 39/18
[52] U.S. Cl. ...................................... 424/89; 195/1.4; 195/1.5
[58] Field of Search ...................... 424/89; 195/1.4, 1.5

[56] References Cited

U.S. PATENT DOCUMENTS

| | | | |
|---|---|---|---|
| 3,149,036 | 9/1964 | Woodhoor et al. | 424/88 |
| 3,519,400 | 7/1970 | Anderson | 23/309 |
| 3,847,737 | 11/1974 | Kanarak | 195/1.4 |

FOREIGN PATENT DOCUMENTS

| | | |
|---|---|---|
| 277937 | 11/1965 | Australia. |
| 2333M | 2/1964 | France. |
| 974625 | 11/1964 | United Kingdom. |
| 1140316 | 8/1967 | United Kingdom. |
| 1183506 | 3/1970 | United Kingdom. |

OTHER PUBLICATIONS

Corbel et al., J. Hyg. 68:77–80, 81–95 (1970) Degradation of Influenza Virus by Non–Ionic Detergent, Soluble Antigens Obtained From Influenza Virus by Treatment with Non–Ionic Detergent.
Cline et al., Nature 212:487–489 (1966) Improved Continuous Flow Centrifugation With Banding.
Anderson et al. C.A.72 #28717z 28618a #63431y, (1970), C.A. 66 #8701s (1967).
Anderson et al., Analytical Biochemistry 32:460–494; 495–511 (1969).
Reimer et al., Science 152:1379–1381, Jun. 3, 1966, Influenza Virus Purification with the Zonal Ultra–Centrifuge.
Reimer et al., J. Bact. 92:1271–1272, Oct. 1966, Comparison of Techniques for Influenza Virus Purification.
Reimer et al., J. Virol., vol. 1, No. 6:1207–1216, Dec. 1967, Purification of Large Quantities of Influenza Virus by Density Gradient Contrifugation.

*Primary Examiner*—Shep K. Rose
*Attorney, Agent, or Firm*—Bacon & Thomas

[57] ABSTRACT

Virus sub-unit vaccines which are substantially free from pyrogens, virion nucleic acids and unwanted antigenic material are prepared by introducing inactivated whole virus into a continuous loading zonal ultracentrifuge provided with a density gradient containing a haemolytic surfactant and binding the split sub-units isopycnically. All ether-sensitive viruses can be used, especially influenza virus.

16 Claims, No Drawings

PREPARATION OF VIRUS SUB-UNIT VACCINES

This is a continuation, of application Ser. No. 680,756, filed Apr. 27, 1976, now abandoned, which in turn is a continuation of Ser. No. 515,467, filed Oct. 17, 1974, now abandoned.

This invention relates to the preparation of pyrogen free virus sub-unit vaccines, in particular influenza vaccines.

The influenza vaccines generally used at present are inactivated whole virus vaccines which contain, besides the influenza virions, some egg protein derived from the allantoic fluid in which the virus is harvested. On injection, this type of vaccine can give rise to hypersensitivity caused by the egg protein and pyrogenic effects caused by the virions.

The influenza virus, and similar viruses of the same type, i.e. orthomyxoviruses and paramyxoviruses, are characterised by an outer membrane carrying "spikes" of antigens having haemagglutinating and neuraminidase activity. This outer membrane is capable of being disrupted by solvents such as ether or by surfactants to release as sub-units such antigens having haemagglutinating and neuraminidase activity. The so-called 'split virus' vaccines which have hitherto been prepared in this way are found to have lower pyrogenicity than corresponding whole virus vaccines even though no attempt has been made to separate the antigens having neuraminidase and haemagglutinin activity from pyrogens and other unwanted material such as other antigens and nucleic acids.

We have found, however, that the antigens having haemagglutinating and neuraminidase activity are not themselves pyrogenic or otherwise toxic and that consequently a still further reduction in pyrogenicity can be achieved by obtaining the desired antigens substantially free from other unwanted material.

We have attempted to separate the components of a split virus preparation by zonal ultracentrifugation. Batchwise loading of an ultracentrifuge rotor was however found to be impracticable for large scale production and it was found necessary to use a continuous loading zonal centrifuge wherein the relatively dilute suspension of the virus subunits is passed into the rotor and flows across the centripetal end of a concentration gradient. It was found, however, that the very small particles of the desired antigens having haemagglutinin and neuraminidase activity were reluctant to transfer onto the gradient at flow rates consistent with large scale production.

We have now found, however, that viruses of the influenza and associated types, which can readily be introduced into the gradient of a continuous loading zonal ultracentrifuge, can successfully be split while passing through the gradient if a surfactant is present in the gradient solution. This facilitates the large-scale preparation of sub-unit vaccines substantially free from egg protein, pyrogens and virion nucleic acids and containing substantially only the desired protective antigens having haemagglutinin and neuraminidase activity. The haemagglutinin found in the so-called 'spikes' is itself split by the surfactant to a monovalent form which no longer exhibits haemagglutination but does possess the required antigenic properties.

In general, all the ether-sensitive viruses can be split by treatment with detergents and in addition to the above ortho and para myxoviruses, the following viruses can yield sub-unit vaccines, containing protective antigenic components analogous to haemagglutinin and neuraminidase, namely:

(a) Togaviruses
(b) Rhabdoviruses
(c) Leukoviruses
(d) Coronoviruses
(e) Arenoviruses
(f) Herpesviruses
(g) Poxviruses According to one feature of the present invention, therefore, we provide a process for the preparation of a virus sub-unit vaccine derived from an ether-sensitive virus and being substantially free from pyrogens, virion nucleic acids and unwanted antigenic material, including the step of introducing a liquid medium containing the inactivated whole virus into a continuous loading zonal ultracentrifuge provided with a density gradient solution containing a haemolytic surfactant whereby the virions enter the density gradient and are split by the surfactant and the protective antigenic sub-units are banded isopycnically, the fraction or fractions containing the protective antigenic component(s) subsequently being recovered.

While it is possible to load the whole virions directly from a relatively dilute culture medium such as allantoic fluid, it is generally preferred to effect some purification of the whole virus preparation before splitting on the ultracentrifuge.

For such purification, the whole intact, inactivated virus may be isolated using conventional means. Thus, for example, influenza virus may be grown in 10 to 11 day old embryonated hens eggs. The harvested allantoic fluid may then be treated, eg. with $\beta$-propiolactone and/or formalin, to inactive or "kill" the virus and then clarified by centrifugation, e.g. in a Westphalia (trade mark) continuous flow centrifuge.

The virus may then be further purified. While this can be achieved using continuous sedimentation centrifugation, treatment with fluorocarbons, gel filtration or adsorption onto red cells or minerals such as barium sulphate and subsequent elution, it is preferred for speed and ease of handling in bulk to use continuous zonal centrifugation, for example using a KII apparatus (originated in the Molecular Anatomy Program, Oak Ridge National Laboratory, Oak Ridge, Tenn. 37830, U.S.A. and described by Anderson et al. in Analytical Biochemistry 32, 460–494 and 495–511 (1969), and available from Electro-Nucleonics, Inc., 368 Passaic Avenue, Fairfield, N.J. 07006 U.S.A.

A KII rotor of 3.2 liters capacity with a sucrose density gradient is particularly effective. The method used may be that of Reimer et al (Journal of Virology Vol. 1, No. 6 pages 1207–1216). After purification the fractions containing virions, as determined by haemagglutination titre may then be pooled and diluted or dialysed to reduce the density to a level suitable for introduction onto a gradient in the second ultracentrifugation step.

For the step of splitting the virus, the virions are loaded, preferably after purification as described above, onto the density gradient solution of a continuous loading zonal ultracentrifuge. As for the virus purification, a convenient medium for the gradient is a solution of a sugar, in particular sucrose, preferably in buffered saline at a suitable pH for the virus. In general a pH of a little above 7 is desirable and it is convenient to use 0.01 M phosphate as buffer at pH 7.2. A density gradient of about 1.02 to about 1.24 g/ml is suitable. Other solutions which can be used to form a density gradient of this order include polyols such as glycerol and salts such as tartrates or caesium chloride. The gradient may be prepared by half filling the rotor with a solution at the lowest density of the desired gradient and adding an equal volume of a solution at the highest density. Spinning of the rotor at moderate speeds will then establish the gradient.

As stated above, the density gradient solution contains a surfactant in order to split the virus while it traverses the gradient. In general, the surfactant, in aqueous solution, may be introduced into the gradient and the rotor centrifuge is spun for a time to ensure penetration of the surfactant into the gradient solution. Alternatively, the surfactant may be present in the gradient solution when it is loaded into the rotor. Many of the haemolytic surfactants which may be used in this invention form distinct bands in the gradient although banding is not an essential characteristic. The position of the band on the gradient is not critical since the virions, being relatively dense, will traverse the gradient until they reach this band; after splitting, subunits may move to zones of appropriate density which may be on the low density side of the surfactant band.

As stated, the surfactant should be a haemolytic surfactant. By this we mean a surfactant which will give a positive result in the following test:

Chick red blood cells (0.5% V/V in 0.01 M phosphate buffered saline pH 7.0; 0.25 ml) are added to a 1% W/V aqueous solution of the surfactant (0.25 ml). For a positive result, complete haemolysis must occur within 5 minutes at 22° C.

Included within this category are the following types of surfactant:

| | | NONIONICS |
|---|---|---|
| | | Aryl Ether Adducts of Ethylene Oxide |
| | General names: | Alkyl Phenol Ethylene Oxide Condensates or |
| | | Alkyl Phenol polyoxyethylenes or |
| | | Polyethoxy Alkyl Phenols |
| e.g. | Nonidet P40 | Octyl Phenol Polyoxyethylene (Shell) or |
| | | Polyethoxy octyl phenol |
| | Tergitol NPX | Nonyl Phenol 10.5 oxyethylene (Union Carbide) or |
| | | 10.5 Ethoxy nonyl phenol |
| | Triton N101 | Nonyl Phenol 9–10 oxyethylene (Rohm & Haas) or |
| | | 9–10 Ethoxy nonyl phenol |
| | Renex 698 | Nonyl phenol 9–9.5 oxyethylene (Atlas) or |
| | | 9–9.5 Ethoxy nonyl phenol |
| | Belloid EMP | Octyl phenol polyoxyethylene (Geigy) or |
| | | Polyethoxy octyl phenol |
| | Adinol C0630 | Polyoxyethylene nonyl phenol (Fine DyeStuffs) |
| | | Aliphatic Ether Adducts of Ethylene Oxide |
| | General names | Aliphatic Alcohol Polyoxyethylenes or |
| | | Polyethoxy Aliphatic Alcohols |
| e.g | Brij 96 | Oleyl alcohol 10 oxyethylene (Atlas) or |
| | | 10 Ethoxy oleyl alcohol |
| | Tergitol TMNIO | Trimethylnonanol 10 ethylene oxide |
| | Tergitol 15-S-7 | Linear alcohol $C_{11}$ to $C_{15}$ 7-ethylene oxide |
| | | Ester Adducts of Ethylene Oxide |
| | General names | Fatty acid ester Polyoxyethylenes or |
| | | Polyethoxy esters of fatty acids |
| e.g | Cithrol 4ML 400 | Polyethylene Glycol monolaurate (Croda) or |
| | | Lauric acid 400 Polyethylene glycol ester |
| | | Amine Adducts of Ethylene Oxide |
| | General names | Fatty Amine Polyoxyethylenes or |
| | | Polyethoxy Fatty Amines |
| e.g. | Ethomeen 18/25 | Stearyl Amine 15 Oxyethylene (Armour) or |
| | | 15 Ethoxy Stearyl amine |
| | Ethomeen C/25 | Coco Fatty amines 15 oxyethylene (Armour) or |
| | | 15 Ethoxy Coco fatty amines (Av. Mol. Wt. 860) |
| | Ethomeen S/15 | Soya fatty amines 5 oxyethylene (Armour) or |
| | | 5 Ethoxy soya fatty amines |
| | | Alkanolamide Adducts of Ethylene Oxide |
| | General names | Alkanolamide Polyoxyethylenes or |
| | | Polyethoxy Alkanolamides |
| e.g. | Conox J 754 | Exact composition not known |

| | -continued | |
|---|---|---|
| | ANIONICS | |
| e.g. | Texapon N25/5 | Sodium Salt of sulphated lauryl (Dehydag) alcohol dioxyethylene or Dioxyethylene sodium lauryl sulphate |
| | Adinol T | Sodium N-methyl N-oleyl taurine |
| | Solumin T 45S | Sodium Salt of Sulphonated fatty alcohol 45 oxyethylene or 45 Ethoxy fatty alcohol sodium sulphonate |
| | Teepol 610 | Sodium secondary alkyl sulphate (Shell) |
| | Sodium deoxycholate | Anionic bile salt |
| | Pentrone A4 | Amine salt of alkyl aryl sulphonic acid (Glover) |
| | MISCELLANEOUS | |
| e.g. | Belloid M3 | Polyoxyethylene 3 condensate (Geigy) with an aliphatic alcohol |
| | Galoryl MT5 | (CFPT: France) |

In general, the minimum effective quantity of surfactant should be used, to reduce problems of removal later on. For the preferred surfactant, an aryl ether adduct of ethylene oxide, especially Triton N101, the overall concentration in the gradient is preferably at least 0.5% v/v, advantageously 1.0% v/v. The concentration in the localised band on the gradient will, of course, be higher than this. Some surfactant will normally be present throughout the gradient where desired sub-units of the virions band and this prevents or minimises reaggregation of the sub-units. If such aggregation occurs the separation from unwanted antigenic material is poor.

The medium containing the purified virions is then flowed through the zonal ultracentrifuge so that they enter the gradient and are split by the surfactant, eventually banding as separated sub-units. In general, the virions should be loaded at a rate of about 2.8 rotor volumes per hour e.g. about 10 liters per hour for a 3.6 liter KII rotor. (When purifying virions, without splitting, the loading rate may be higher e.g. 30 liters per hour). In general the rotation speed during loading of the gradient may be at least 20,000 r.p.m., conveniently 35,000 r.p.m. giving 90,000 g in the KII centrifuge. After completion of "loading", the ultracentrifuge rotor is spun for a further period, e.g. 2 to 3 hours, to further separate and consolidate the bands and, after the rotor has been slowly decelerated and brought to a halt, the contents of the gradient are run off in fractions. Those fractions containing the desired subunits may then be pooled.

In the case of viruses liberating neuraminidase, or analogous material this may be detected by standard assay methods, e.g. the method of Warren (J. Biol. Chem 234, 1959, p 1971). In the case of viruses liberating mono-valent haemagglutinin, or analogous material this cannot be identified by assay of haemagglutination as the haemagglutinin obtained is in the monovalent form and does not exhibit such activity. It is necessary, therefore, to assay the antigenic effect of the samples (e.g. by the haemagglutination inhibition titre of the single radial diffusion test) or measure a phsical characteristic such as optical density, u.v. absorption etc. In some cases haemagglutinin will be found in the same fractions as neuraminidase.

The virus used is ether-sensitive and as such will have the necessary strippable coat containing antigenic material. The preferred virus is an influenza virus, but other suitable viruses include measles and mumps in humans and Newcastle Disease virus (NDV) in poultry (which are all myxoviruses) and bovine rhinotracheitis virus (which is a Herpes virus).

For use as a vaccine, the pooled antigenic sub-unit fractions must be substantially free from any surfactant and this can be achieved in the case of non-ionic surfactants, such as Triton N101, by depression of the cloud point by addition of ionic material to the diluted aqueous medium so that the surfactant separates as a new phase. However, it is found advantageous to separate the sub-units by selective adsorption onto colloidal aluminium hydroxide (e.g. 'Alhydrogel') leaving the surfactant in solution. This process can desirably be effected as a second step after cloud-point depression, where applicable. The use of the aluminium hydroxide has the advantage that the antigens are obtained in an adjuvanted form which is usable as a vaccine as such. Alternatively, the antigens may, after removal of surfactant, be adjuvanted with other convenient adjuvants such as oil emulsions e.g. emulsions of water in an oily fatty acid glyceride such as peanut oil. Such emulsions may contain non-ionic emulsifiers such as sorbitan trioleate and a stabiliser such as aluminum monostearate.

The potency of 'Alhydrogel'-adsorbed influenza subunit vaccine was compared with aqueous whole influenza virion vaccine. The results are shown in the following Table. The potency was estimated by inoculating groups of 5 chickens intramuscularly in the leg with 0.5 ml of vaccine dilutions on day 0 and day 14 and bleeding on day 28. Haemagglutination inhibition and antineuramaminidase antibodies were estimated.

TABLE

| VACCINE (influenza virus strain A/ Hong Kong/1/68X) | Haemagglutination Inhibition Titre Geometric Mean Titre (GMT) | | Anti Neur- aminidase Titre G.M.T. |
| --- | --- | --- | --- |
| | 2 weeks | 4 weeks | 4 weeks |
| Whole virus aqueous single strength | 291 | 2027 | 75 |
| Whole virus aqueous 1 in 4 dilution | 22 | 582 | 27 |
| Whole virus aqueous 1 in 10 dilution | 11 | 291 | 0 |
| whole virus aqueous 1 in 100 dilution | 0 | 6 | 0 |
| Sub-unit adsorbed single strength | 167 | 1536 | 137 |
| Sub-unit adsorbed 1 in 4 dilution | 24 | 1536 | 26 |
| Sub-unit adsorbed 1 in 10 dilution | 1 | 1163 | 36 |
| Sub-unit adsorbed 1 in 100 dilution | 0 | 18 | 0 |

Single strength aqueous virus, based on haemagglutination titre, contained 400 i.u./ml. The single strength sub-unit vaccine contained an equivalent amount of antigen. These results show that the sub-unit adsorbed vaccine is similar or better in antigenicity than whole virus aqueous vaccine.

According to a further feature of the present invention, therefore, we provide a process for the preparation of an adjuvanted virus sub-unit vaccine containing protective antigenic components and being substantially free from pyrogens nucleic acids and unwanted antigens including the step of adsorbing onto colloidal aluminium hydroxide the required protective antigenic component(s) obtained by the foregoing procedure according to the invention, preferably after first removing most of any remaining surfactant. Non-ionic surfactants may, for example, be removed by cloud-point depression.

The colloidal aluminium hydroxide used conveniently contains about 2% as $Al(OH)_3$, e.g. Alhydrogel. The final concentration of the 2% aluminium hydroxide gel in the vaccine should, in general, preferably be from 6.0% to 18% v/v, preferably about 12.5% v/v. The adsorbed vaccine may, if desired, be washed free of any associated impurities, e.g. residual surfactant, by centrifuging the aluminium hydroxide and resuspending in fresh phosphate buffered saline. The optimum pH for the pH for the final vaccine is from 7 to 8, advantageously about 7.6.

The following Examples illustrate the invention further.

EXAMPLE 1

Influenza virus strain A/Hong Kong/1/68X was grown in 11 day old embryonated hens eggs. The allantoic fluid was harvested after 48 hours, inactivated with β-propiolactone (1 ml per 1000 ml allantoic fluid) overnight at room temperature and then clarified through a Westphalia (Trade Mark) continuous flow centrifuge. The clarified inactivated allantoic fluid was flowed at 10 liters per hour over a gradient prepared from 60% w/w sucrose in 0.01 M phosphate buffered saline pH 7.2 (1.8 liters) and pure 0.01 M phosphate buffered saline pH 7.2 (1.4 liters) in a KII rotor. The rotor speed was 35,000 r.p.m. (90,000 g) and it was spun for 2 hours after all the allantoic fluid has been introduced. The fractions containing the influenza virions as determined by their haemagglutinin titre, were pooled (13,500 i.u. per ml; 1500 ml total).

The virions were present in the fractions containing 40% w/w sucrose, and were diluted 1 in 8 in 0.01 M phosphate buffered saling pH 7.2 to a sucrose concentration of 5% w/w. The diluted virions were flowed over a sucrose gradient containing 1% Triton N101 in the KII rotor at 10 liters per hour. The sucrose gradient was prepared by filling the stationary rotor with 1.8 liters of 60% w/w sucrose in 0.01 M phosphate buffered saline pH 7.2 also containing Triton N101 (1% v/v) and 1.4 liters of 0.01 M phosphate buffered saline pH 7.2 on top and then accelerating the rotor to 90,000 g (35,000 r.p.m.). The rotor was spun at 35,000 r.p.m. for 2 hours after all the influenza virus had been introduced. The fractions containing the large neuraminidase and Triton peak were pooled; heamagglutinin was also present (50% of original level by the haemagglutinin titre. To 3 parts of this pool was added 1 part of 1.6 M phosphate buffer pH 7.6. The mixture became cloudy and the phases were separated by spinning at 2000 g for 20 mins. The lower phase was collected and contained the neuraminidase and hemagglutinin with only about 0.05% v/v Triton N101 (yield 40%). To an aliquot (10 ml) of this an equal volume of 'Alhydrogel' was added and the mixture allowed to adsorb overnight at 4° C. Dilutions were made and the potency of the dilutions estimated in chickens. After the dilution to give a vaccine of adequate potency had been determined, all the vaccine was diluted to this strength but the final 'Alhydrogel' concentration was kept at 12.5%. Before the vaccine was adjuvanted the potency was estimated by the single radial diffusion method of Schild. (J. Gen. Virology. 16 (1972) 231–236).

EXAMPLE 2

The process of Example 1 was repeated except that Ethomeen 18/25 replaced Triton N101 in the gradient.

EXAMPLE 3

The process of Example 1 was repeated but the Triton N101 was not separated by cloud-point depression. Instead, to the fractions from the KII centrifuge containing the haemagglutinin, neuraminidase and Triton N101 was added 12.5% v/v 'Alhydrogel'. The mixture was left at 4° C. overnight and the 'Alhydrogel' spun off. The supernatant contained the Triton N101. The pellet was suspended in its original volume of 0.01 M phosphate buffered saline pH 7.2, spun and the pellet resuspended in its original volume of 0.01 M phosphate buffered saline. The potency of the vaccine was determined, as in Example 1 and the vaccine diluted accordingly keeping the final 'Alhydrogel' concentration 12.5 v/v.

EXAMPLE 4

The process of Example 1 was repeated with influenza virus strain B/Hong Kong/8/73 to give a potent vaccine.

EXAMPLE 5

The process of Example 1 was repeated with influenza virus strain B/Victoria/98926/70 to give a potent vaccine.

EXAMPLE 6

The process of Example 1 was repeated with influenza virus strain A/England/42/72 to give a potent vaccine.

EXAMPLE 7

Newcastle Disease virus was grown in 10 day old embryonated hens eggs. The allantoic fluid was harvested after 96 hours, inactivated with $\beta$-propiolactone (1 ml per 1,000 ml fluid) for 2 hours at 37° C. The solution was centrifuged at 10,000 g at a flow rate of 20 liters per hour to clarify and remove urates from the solution.

The clarified allantoic fluid was flowed over a sucrose gradient prepared as in Example 1 in the KII rotor at 10 liters per hour. The rotor was centrifuged at 35,000 r.p.m. for 2 hours after all the allantoic fluid had been introduced. The fractions containing the subunits, as determined by neuraminidase content, were pooled. The rest of the method was as for Example 1.

EXAMPLE 8

The fractions containing influenza neuraminidase and haemagglutinin from Example 1 after the Triton N101 had been removed by cloud-point depression were pooled and diluted with 0.01 M phosphate buffered saline pH 7.2 to give a fluid containing 1600 i.u. of haemagglutinin per ml. It was then homogenised in the following proportions.

Virus subunits fluid—39.5 ml
Vegetable oil—53 ml
Sorbitan trioleate—5 ml

Aluminium monostearate—2.5 ml (The aluminium monostearate was heated in the vegetable oil to disperse and the sorbitan trioleate added before mixing with the aqueous phase). The antigenicity of this vaccine was confirmed in chickens.

We claim:

1. A process for the preparation of a virus sub-unit vaccine derived from an ether-sensitive virus and being substantially free from pyrogens virion nucleic acids and unwanted antigenic material, including the step of introducing a liquid medium containing the inactivated whole virus into a continuous loading zonal ultracentrifuge provided with a density gradient solution containing a haemolytic surfactant, whereby the virions enter the density gradient and are split by the surfactant and the antigenic sub-units are banded isopycnically, the fraction or fractions containing the protective antigen sub-units subsequently being recovered.

2. A process as claimed in claim 1 in which a continuous loading zonal ultracentrifuge of the KII type is used.

3. A process as claimed in claim 1 in which the density gradient solution is a colution of sucrose in buffered saline.

4. A process as claimed in claim 1 in which the density range of the density gradient is from 1.02 to 1.24 g/ml.

5. A process as claimed in claim 1 in which the surfactant is an aryl ether adduct of ethylene oxide.

6. A process as claimed in claim 5 in which the surfactant is nonyl phenol 9–10 oxyethylene.

7. A process as claimed in claim 6 in which the overall concentration of the surfactant in the gradient is at least 0.5% v/v.

8. A process as claimed in claim 7 in which the concentration of the surfactant is about 1%.

9. A process as claimed in claim 1 in which the virus is an infuenza virus.

10. A process as claimed in claim 1 in which the virus is a Herpes, mumps, measles or Newcastle Disease virus.

11. A process as claimed in claim 1 in which a non-ionic surfactant is removed from the suspended protective antigenic sub-units by separation as a further phase by adjusting the ionic strength of the suspension to the cloud point of surfactant.

12. A process as claimed in claim 1 in which the virus sub-units are subsequently formulated with a vaccine adjuvant.

13. A process as claimed in claim 12 in which the protective antigenic sub-units are both purified and adjuvanted by selective adsorption onto colloidal aluminium hydroxide.

14. A process as claimed in claim 13 in which the colloidal aluminium hydroxide contains about 2% as $Al(OH)_3$ and the concentration of the colloidal aluminium hydroxide in the vaccine is from 6.0% to 18% v/v.

15. A process as claimed in claim 12 in which the adjuvant is an emulsion of water in an oily fatty acid glyceride.

16. A process as claimed in claim 12 in which the adjuvant is an emulsion of water in peanut oil containing sorbitan tri-oleate as emulsifier and aluminium monostearate as stabliser.

* * * * *